United States Patent [19]
van den Haak

[11] Patent Number: 5,380,286
[45] Date of Patent: Jan. 10, 1995

[54] SAFETY DEVICE FOR AN INJECTION SYRINGE NEEDLE

[75] Inventor: Abraham van den Haak, Eesergroen, Netherlands

[73] Assignee: Advanced Protective Injection Systems B.V.

[21] Appl. No.: 224,111

[22] Filed: Apr. 6, 1994

Related U.S. Application Data

[60] Continuation of Ser. No. 818,187, Jan. 8, 1992, abandoned, which is a division of Ser. No. 490,568, Apr. 26, 1990, Pat. No. 5,116,319.

[30] Foreign Application Priority Data

Aug. 23, 1988 [NL] Netherlands ............... 8802106

[51] Int. Cl.$^6$ .................... A61M 5/50; A61M 5/32
[52] U.S. Cl. .................... 604/110; 604/195; 604/243
[58] Field of Search ............. 604/110, 192, 195, 196, 604/198, 240-243, 263

[56] References Cited

U.S. PATENT DOCUMENTS

| | | | |
|---|---|---|---|
| 4,664,653 | 5/1987 | Sagstetter et al. | 604/197 |
| 4,710,170 | 12/1987 | Haber et al. | 604/110 |
| 4,747,829 | 5/1988 | Jacob et al. | 604/110 |
| 4,799,927 | 1/1989 | Davis et al. | 604/192 |
| 4,826,484 | 5/1989 | Haber et al. | 604/110 |
| 4,826,489 | 5/1989 | Haber et al. | 604/195 |
| 4,838,869 | 6/1989 | Allard | 604/195 |
| 4,898,589 | 2/1990 | Dolgin et al. | 604/198 |
| 4,904,242 | 2/1990 | Kulli | 604/110 |
| 4,909,794 | 3/1990 | Haber et al. | 604/195 |
| 4,919,657 | 4/1990 | Haber et al. | 604/232 |
| 4,931,040 | 6/1990 | Haber et al. | 604/110 |
| 4,935,014 | 6/1990 | Haber | 604/195 |
| 4,944,723 | 7/1990 | Haber et al. | 604/110 |
| 4,950,251 | 8/1990 | Haining | 604/195 |
| 4,955,870 | 9/1990 | Ridderheim et al. | 604/195 |
| 4,957,490 | 9/1990 | Byrne et al. | 604/197 |
| 4,957,589 | 9/1990 | Yamada | 156/643 |
| 4,978,340 | 12/1990 | Terrill et al. | 604/195 |
| 4,986,813 | 6/1991 | Blake, III et al. | 604/110 |
| 5,007,803 | 4/1991 | Ellard | 604/195 |
| 5,084,018 | 1/1992 | Tsao | 604/110 |

FOREIGN PATENT DOCUMENTS

| | | |
|---|---|---|
| 0272035 | 6/1988 | European Pat. Off. . |
| 0276160 | 7/1988 | European Pat. Off. . |
| 0278493 | 8/1988 | European Pat. Off. . |
| 0282097 | 9/1988 | European Pat. Off. . |
| 0288003 | 10/1988 | European Pat. Off. . |
| WO89/02760 | 4/1989 | WIPO . |

Primary Examiner—John D. Yasko
Assistant Examiner—Adam J. Cermak
Attorney, Agent, or Firm—Kenyon & Kenyon

[57] ABSTRACT

A safety device for an injection syringe comprising an outer casing (1) defining an injection fluid space with a plunger (11) movable therein, said plunger being adapted to be coupled with a plunger rod (6) provided with an actuating knob or ring, while at the opposite end of said casing a needle foot (16) equipped with a hollow needle (15) may be fixed thereto in such a manner that the needle bore communicates with the interior of the fluid space, the needle foot (16) being movable inwards relative to the outer casing and adapted to be coupled to the piston in order that the needle may be retracted into said outer casing; the needle foot (16) and the casing (1) are provided with mutually engageable locking means for locking the needle foot (16) in its non-retracted position, and the plunger (11) or the plunger rod (6) and the needle (15) or the needle foot (16) are provided with means for coupling the plunger (11) or plunger rod (6) with the needle (15) or needle foot (16) and releasing the needle or needle foot lock after the plunger (11) has been completely pushed all the way into the injection fluid space (1. 10).

2 Claims, 7 Drawing Sheets

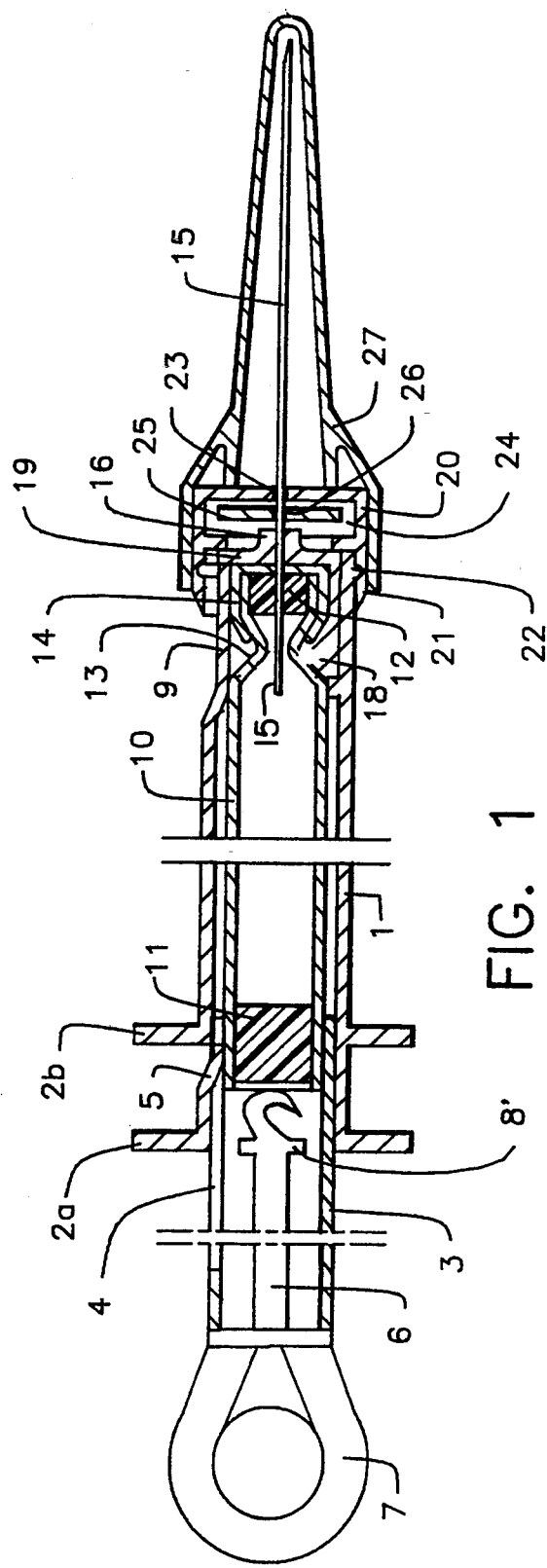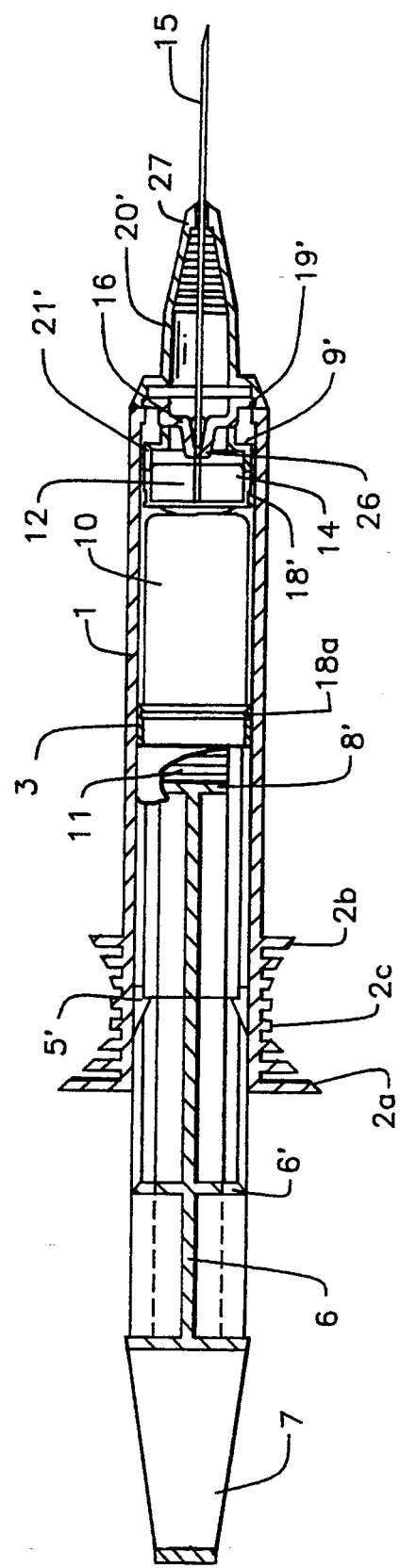

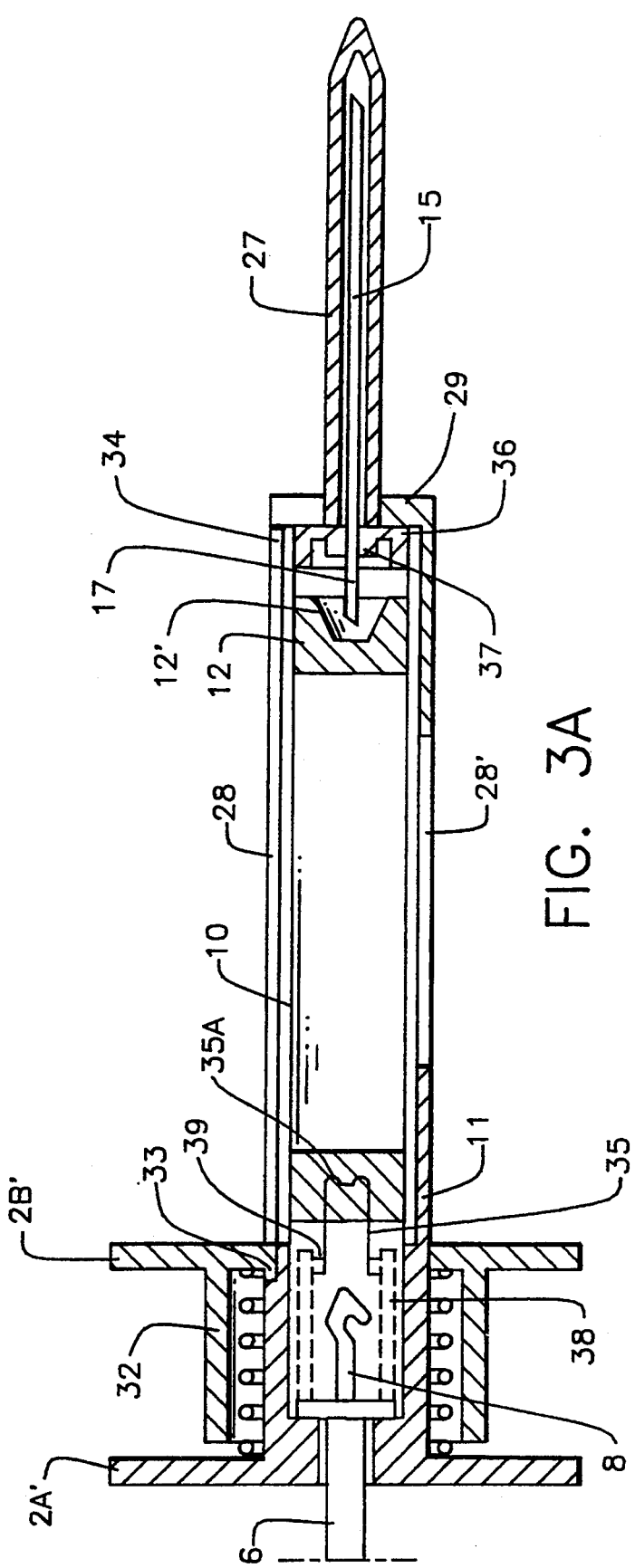
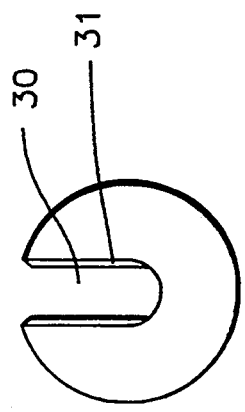
FIG. 3A
FIG. 3B

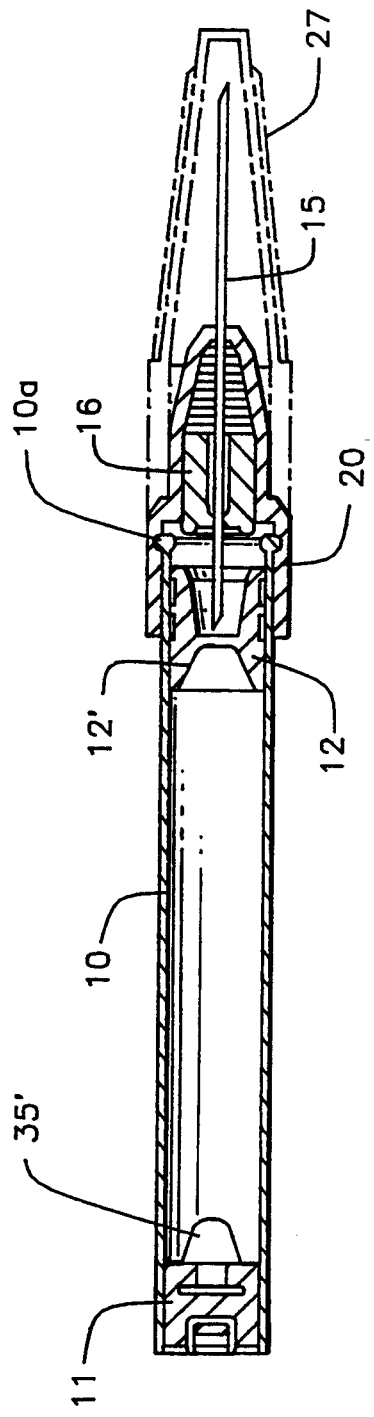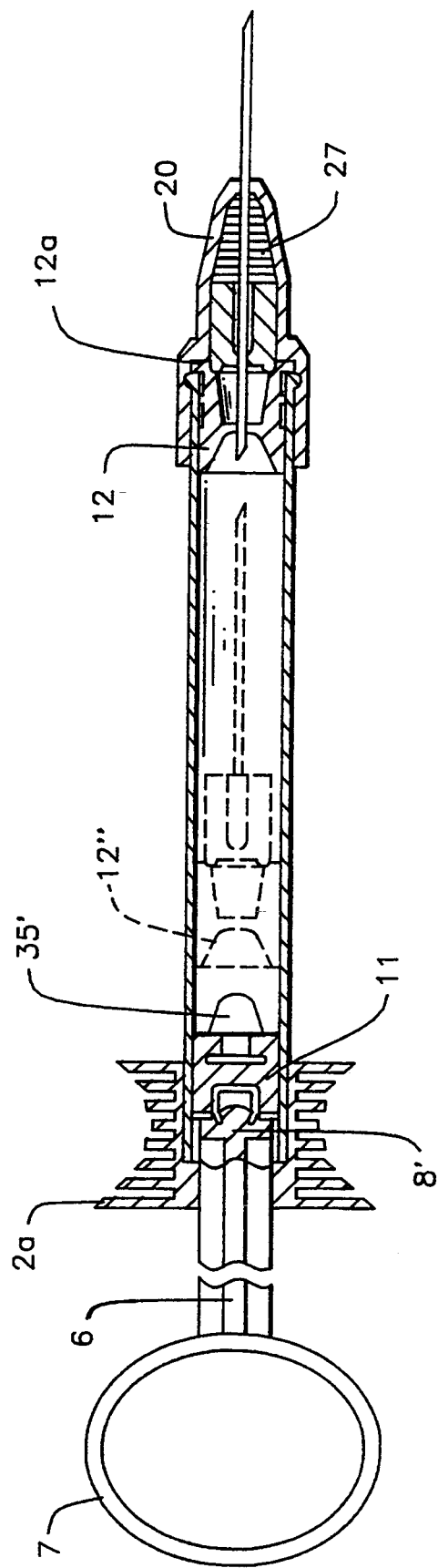
FIG. 4A
FIG. 4B

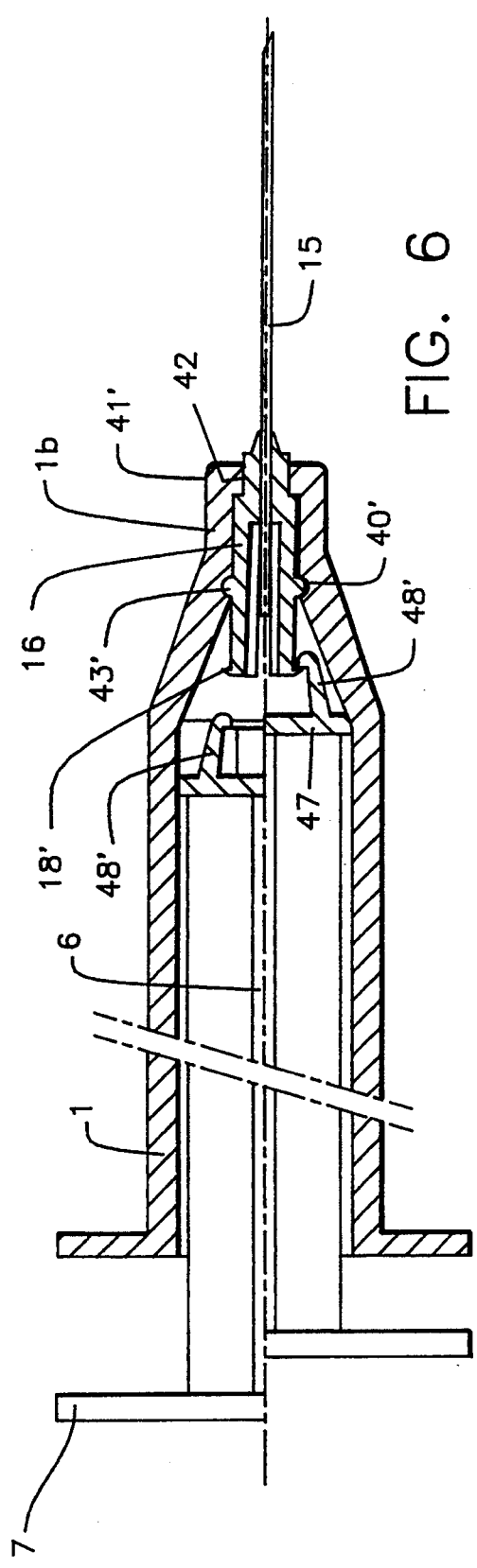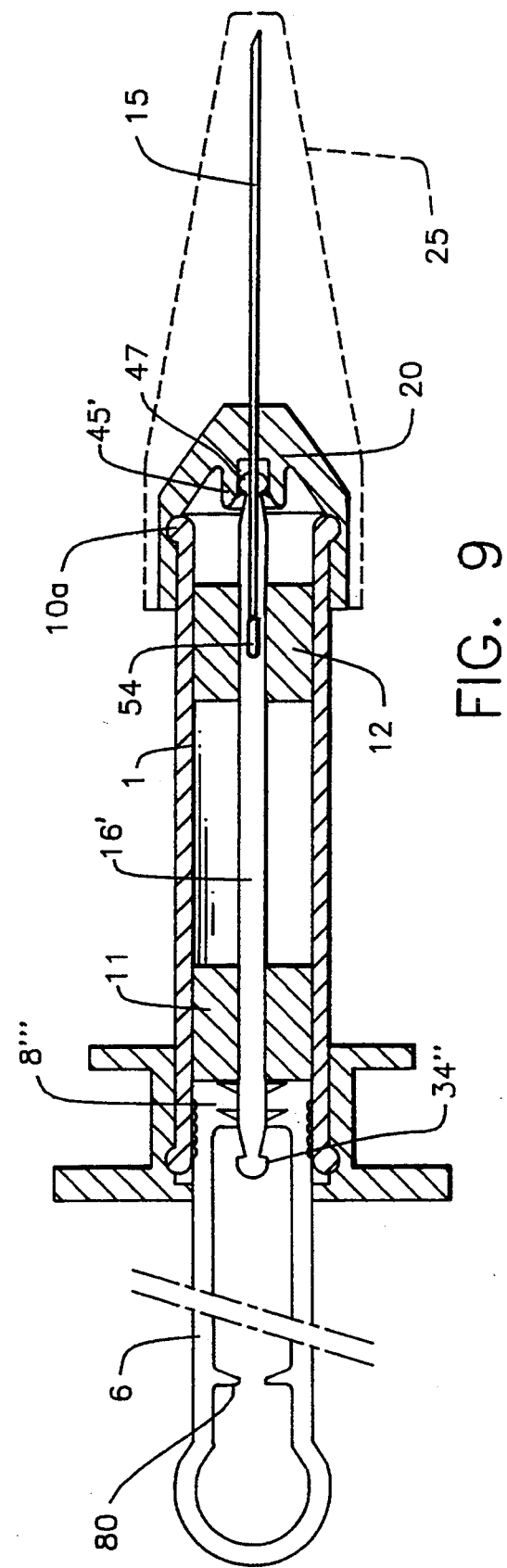

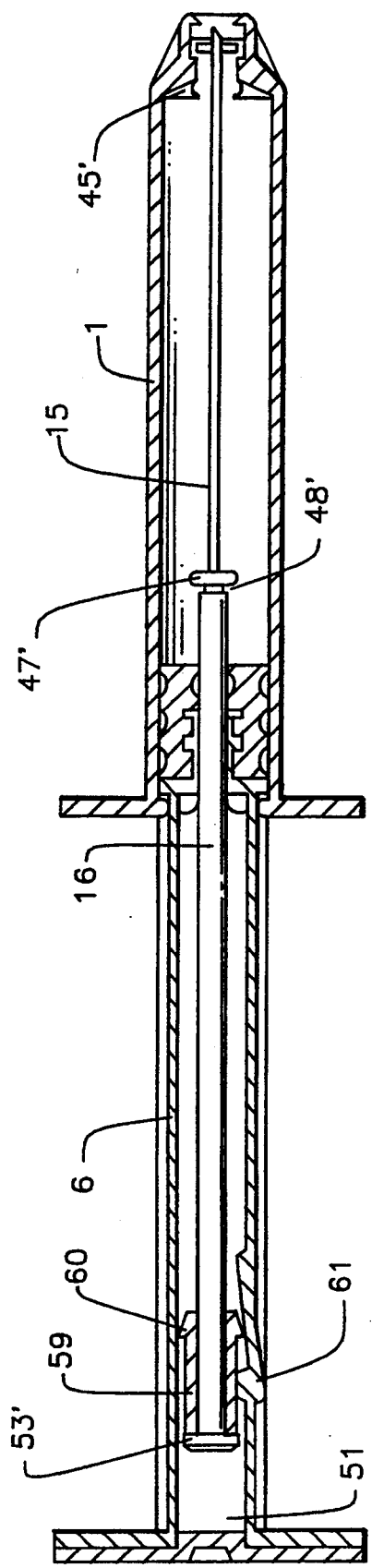
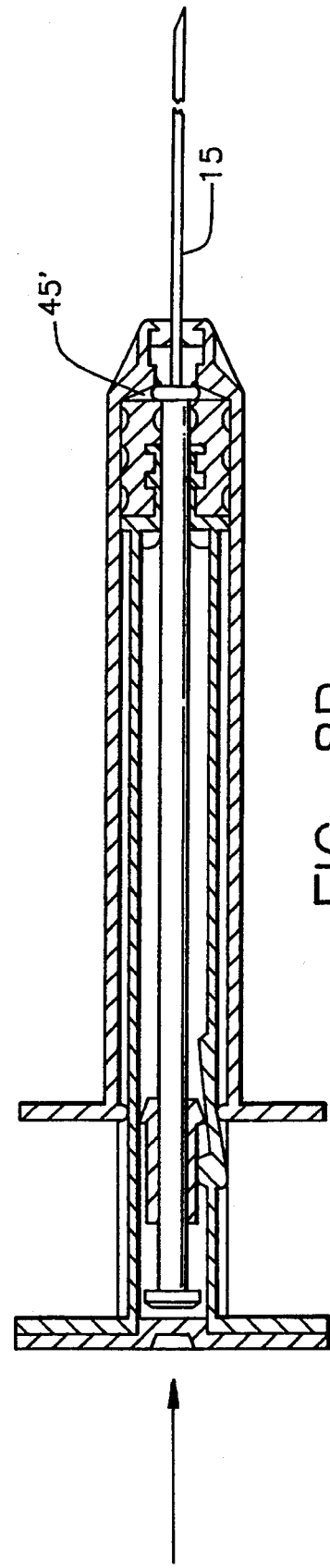

SAFETY DEVICE FOR AN INJECTION SYRINGE NEEDLE

This application is a continuation of U.S. Ser. No. 07/818,187, filed Jan. 8, 1992 (now abandoned), which in turn is a division of U.S. Ser. No. 07/490,568, filed Apr. 26, 1990 now U.S. Pat. No. 5,116,319, issued May 26, 1992, based upon PCT/NL89/00064, filed Aug. 23, 1989 and which designated The United States.

There is an increasing demand for injection syringes the needle of which can be covered after use in order to prevent injury by a used needle. On or in a needle which has been used for an injection there may be blood residues which, if another person pricks himself with the needle, may lead to infection with serious diseases, more particularly as yet incurable and even deadly diseases.

Replacing the sleeve used for packaging a needle after use is not a satisfactory solution, since injury may occur particularly in the course of fitting such a narrow sleeve especially if the needle is stuck outside the opening. Used needles by themselves or as part of an injection fluid container unit or an entire syringe are generally thrown away. Care needs to be taken that the needles stay protected at all times, and thus also during processing of domestic waste. In addition, it is often necessary to prevent re-use of used disposable syringes by professional users as well as drug addicts.

Various solutions to this problem have already been proposed, such as sheaths which are slidable along the syringe, but these do not provide absolute security, because of, i.e., an insufficiently secure locking or fragility of the sheaths. In other solutions, the inside end of the needle, which connects the needle to the cylinder of the syringe, is connected to the plunger so as to be retractable into the cylinder of the syringe after use. To this end, the inside end of the needle is first connected internally to the cylinder, for instance by means of a snap lock. However, connecting the plunger to the inside end of the needle, and sometimes also providing for disengagement of the inside end of the needle from the bottom of the cylinder, requires rotating and sliding movements in a certain order, which complicates the operation of the device. It is however desirable to provide the advantage of rendering the needle harmless by a manual movement which is as simple as possible. According to yet another published proposal, the inside end of the needle is connected to the cylinder by a line of weakness, (weakened section or tear line) which, subsequent to the coupling of the inside end to the plunger by means of a snap lock, must be broken in order to retract the needle into the cylinder. It is difficult to produce such a line of weakness in a properly reproducible and reliable way, and besides, it is possible to move the needle outwards, exposing it again.

The invention provides a syringe which does not have the said disadvantages. The syringe according to the invention comprises an elongate casing having a first end and a second end and an interior surface which defines a chamber for receiving a cartridge; the first end having an opening adapted for slidable engagement with a plunger movable within said chamber including means for preventing removal of said plunger from said chamber and said second end being adapted for engagement with a needle cap; the plunger comprising an actuator handle having a rod and a needle foot engagement means extending therefrom; and a blocking means for preventing a cartridge disposed within said chamber from passing through said opening until said plunger has been passed through said opening into said chamber.

The invention will now be elucidated in greater detail with reference to the accompanying drawing, showing:

FIG. 1 show a first embodiment of a safety syringe according to the invention in longitudinal section;

FIG. 2 show a modification of the syringe of FIG. 1;

FIGS. 3A and 3B show a section corresponding to FIG. 1 and an end view, respectively of a modified embodiment;

FIGS. 4A and 4B show a modification of the embodiment of FIG. 3 in two different conditions;

FIG. 6 shows a modification of the syringe of FIG. 5;

FIGS. 8A to 8D show a modification of the syringe of FIG. 7 in different stages of the operation thereof; and FIG. 9 shows another modification of the syringe of the invention combining features of the syringes of FIGS. 4 and 7.

Figure 5B:
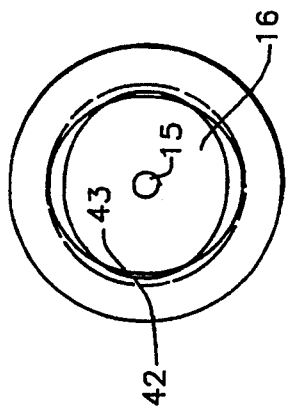
FIGS. 5A and 5B show sections through another embodiment of the safety syringe.

FIG. 1 shows a first embodiment of a syringe with a needle safety cover according to the invention, which is intended to contain closed glass container 10 filled with injection fluid, and which is particularly intended to be used only once. The syringe shown is more especially embodied as a syringe having a plunger 6 which may be retracted after piercing a patient's skin with the point of the needle, 15 in order to establish whether a blood vessel has been hit, which will be apparent if blood is drawn in.

The syringe comprises an outer casing 1 having at least one window (not shown), and with two finger abutment edges 2a and 2b, between which the index and middle fingers are to be placed. Inside this casing, 1 a sleeve 3 is fitted, which is provided with longitudinal grooves 4, in each of which there is a projection 5 of the casing 1, which prevents the sleeve 3 from being removed from the casing. A plunger rod 6 is connected to this sleeve 3, which has, at its outer end, an actuation ring 7. The inner end of the plunger rod 6 has a coupling hook 8.

The other end of the casing 1 is provided with, for instance, three inwardly bent gripping springs 9. These fit grippingly around an injection fluid container 10 of the type which is usual in dental syringes. This container is closed at one end by a rubber stopper 11 which serves as a plunger, into which the hook 8 may be pushed, and embedded to form a push-pull connection with the stopper 11 in a known fashion. The other end is closed by a stopper 12 which may be pierced by the needle inner end 17 which stopper is held by a metal cap 14 fixed in a waisted portion 13 of the container 10. A further part of the syringe is a needle 15, needles of various lengths and/or thicknesses being usable. Each needle is fixed in a needle foot 16, its inner end 17 projecting out of the foot 16, so that it can be pressed through the stopper 12 into the container 10. The foot 16 is provided with resilient claws members 18, which, when the needle foot is applied, engage around the cap 14 and in the waisted portion 13. The edge 19 of the foot 16 then abuts the end faces of the gripping springs 9, which prevent the needle foot from moving inwards.

To use the syringe, the sleeve 3 is retracted as far as possible, after which the container 10 is moved inwards in between the springs 9 until its end closest to stopper 11 enters into the sleeve 3. By keeping the stopper 12 stationary, the hook 8 can be driven into the plunger 11 by pushing the ring 7 inwards. The plunger cannot move inwards, since the stopper 12 will not allow any fluid through. The needle 15 and associated structure including needle foot 16 are then fixed to the other end of the container 10, the needle end 17 penetrating the stopper 12. The syringe is then ready for use.

When the plunger 6 is completely pressed in, and the container 10 is empty, the sleeve 3 reaches the springs 9, which are pressed outwards by the sleeve 3, so that the inward lock of the needle foot 16 is terminated, while the needle end 17 may penetrate into the plunger 11. If the ring 7 is then pulled, the container 10 with the needle foot 16 connected thereto by the gripping members 18 is retracted. The needle 15 and its foot 16 then disappear entirely into the casing 1.

The container 10 with the needle 15 might then be separated from the syringe again in order to be disposed of in, say, a secure collecting container or to be destroyed in a destruction apparatus. It would also possible to place the casing 1 with its opening on a hard surface and then to bend the needle 15 onto itself and to throw away the container only then. It is then no longer possible to push the needle out of the container.

Preferably, however, the needle foot 16 is provided, as shown, with an additional cap 20 which fits around the container, and which is provided with gripping claws 21 which are fixed around the end portion of the casing 1 between the springs 9 behind lugs 22 provided thereon.

The front surface of this cap 20 has a passage 23 for the needle 15. Within this cap 20, there is a ring 25 which, in a manner known per se, is slidable transversely to the needle, so that, after retracting the needle from the ring, this ring having a passage 26 for needle 15 can move downwards under its own weight, so that, when the needle is again pushed outwards, its points hits the ring, and if pressed further the needle is bent onto itself. Thus, the needle can be made harmless without any additional operation.

In embodiments where the needle is placed outside the center line, such as are used for instance for extracting blood, it is also possible to use a cap which is provided with a corresponding hole for the passage of the needle, and which is rotated after retraction to provide an abutment surface for the needle point, while the cap may be provided with a suitable locking device and may particularly be forme as a shiftable needle safety cover.

In their unused state, the cap 20 with the needle foot 16 are inside a protector sheath 27, which is closed in a sterile manner by a cover (not shown). After removal of this cover (in particular, after the pulling away of a sealing strip) the cap 20 can be fitted to the end of the casing, after which the sheath 27 is withdrawn from the cap 20.

FIG. 2 shows a preferred embodiment of the syringe of FIG. 1, and corresponding parts are indicated by the same reference numerals, as the case may be provided with primes to indicate a difference in shape. This syringe is shown with the plunger 11 already partially pushed inwards into the container 10, and the inner needle end 17 has already pierced the stopper 12.

Between the edges 2a and 2b ridges 2c are provided for improving the grip. The cross-shaped plunger rod 6 terminates in a flat disc 8' which is intended to contact the plunger 11 of the fluid container 10.

The container 10 is maintained at its outer end by resilient claws 5' which, after the plunger rod 6 has been completely pressed inwards, will be flexed outwards by a ring-shaped portion 6' of the rod 6 so as to allow the container 10 to be retracted afterwards, as will be explained below.

The end of the casing 1 at the needle side is substantially rigid, and is, at the inside provided with a shoulder 9' behind which resilient retaining the needle foot 16 in a cover (not shown) for providing a sterile package of the needle. The edge 19 of the needle foot fits in a corresponding groove of the cap 20, and the resilient claws 18' of the needle foot 16 lie flatly against the container cap 14, so that a relative sliding movement is possible.

The needle foot 16 is provided with in inwardly directed projection 26 which, as shown, will contact the outer surface of the stopper 12 which is, in fact, a rather elastic membrane. When pressing the plunger 11 inwards for the first time, this stopper 12 will be deformed inwardly by the projection 26, since the flow resistance in the hollow needle 15 is rather high. When the pressure on the plunger rod is relieved, the stopper 12 will return again towards its original position, so that the liquid in the hollow needle will be sucked back, and then it will appear whether blood is sucked in too, indicating that a blood vessel had been hit by the needle. In the case of the syringe of FIG. 1, this aspiration is obtained in the usual manner by retracting the eye 7.

After emptying the container 10, the extremity of the sleeve 3 will slide over the claws 18' of the needle foot, and a groove 18a will engage the claw ends so that the needle foot 16 is coupled with the sleeve 3, and will be retracted together with the sleeve for retracting the needle 15 inside the casing 1. The cap 20 is provided, on its inclined inner surface, with ripples 27. If, then, the plunger rod 6 is pressed inwards again, the tip of the needle will hit these ripples, 27 when the needle is not completely straight, so that the needle will be wrinkled and, thus, destroyed. The needle can be fixed in the needle foot 16 in a slightly inclined manner so as to ensure that the needle will obtain the required inclination.

The cap structure of FIG. 2 including projection 26 can be adapted for use in the embodiment of FIG. 1 and other embodiments disclosed herein.

FIG. 3A shows an alternative embodiment of the syringe according to the invention, intended especially for re-using the syringe casing. The outer casing 1 is, as is the case with syringes in common use, provided with a window 28 which allows the injection fluid container 10 to be loaded sideways. On the opposite side, there is a smaller window 28', which allows the loaded container 10 to be seen through the casing 1 and which also facilitates the ejection of the used container 10.

The end face 29 at the needle end of the casing 1 is, in the embodiment shown, provided with a fitting groove 30 (see FIG. 3B) open towards the window 28 and which serves for fitting the needle foot 36 to the container 10. These containers 10 have a special shape, and form a coherent unit with the needle foot 36 and the needle 15. The needle is surrounded by a protecting sheath 27 attached to the needle foot 36, and the groove 30 has sharp edges 31 which, during fitting of the needle foot 16 in the groove 30, form an incision in the wall of the sheath 27, whereby the sheath 27 can be removed by, for instance, a rotational movement.

To facilitate the fitting of a container 10, the abutment edge 2b is slidable relative to the edge 2a', and is pressed outwards by a spring 32. Retraction of the edge 2b' frees space for the insertion of the container 10 up to a shoulder 33 and the opposite side of shoulder 33 prevents the container 10 from dropping out of the casing 1.

At the needle end, a stopper 12 is provided, which lies sealingly against the inside wall of the container 10, but is slidable therein with a certain friction. In the unused state, the stopper 12' is free from the inner end 17 of the needle 15. After insertion of the container 10, into the syring the plunger rod 6 is pressed in and connected by a hook 8 to the plunger 11 of the container 10. The pressure of the fluid will move the stopper 12, so that the inner end 17 of the needle will penetrate the thinner center postion 12' of of the stopper 12. The fluid can then be ejected through the needle 15.

A metal sleeve 35 with inwardly bent tabs or teeth 35a is embedded in the plunger 11. The needle is guided through an opening 36 in the needle foot and is resiliently gripped. A collar 37 formed on the needle inner end 17 prevents the needle 15 from being pressed outwards during the pressing of the stopper 12.

After the plunger 11 is driven all the way in, the needle inner end 17 penetrates into the plunger and enters between the teeth 35a which engage grippingly around the said needle end 17. If the plunger rod 6 is retracted, these teeth 35 grip the needle end 17 even more strongly, so that the needle 15 is drawn along and can slide in, with a certain friction, through the opening 36.

As soon as the needle 15 is drawn all the way into the container 10, the opening 36 closes at least partially due to the relaxation of the tensions caused by the resilient compression of the foot. If the plunger rod 6 is then pushed inwards, the point of the needle abuts the inner wall of the foot 16, so that the needle 15 can be bent and made unusable.

Instead of a hook 8 at the end of the plunger rod 6, a sleeve 38 can be formed on the end of the rod 6, as indicated in dashed lines, which can engage with the teeth 39 projecting outwards from the sleeve 34 to form the required pulling connection. These teeth may also project inwards in order to engage the outside of the end of the rod 6.

In this embodiment, it is also possible to use separate needles, the foot 16 of which is fitted to tahe end of the container 10, and in which case, instead of a shiftable stopper 12' a penetrable stopper 12 as shown in FIG. 1 may be used, other connections being posible as well.

FIGS. 4A and B show a modification of the syringe of FIG. 3, in which, again, corresponding elements have been indicated with the same reference numerals (as the use may be provided with primes to indicate a difference in shape). A casing 1 (not shown here) can be present as in the case of FIG. 3, but it is also possible to provide the outer wall of the container 10 with a transparent coating for protecting the glass wall thereof against breaking.

The plunger rod 6 shown in FIG. 4B (which may have again a cross-shaped section) is, instead of the hook 8, provided with a stud 8" which co-operates with inwardly directed hooks 39' of a sleeve 34' embedded in the plunger 11, and the rod 6 can be provided as a separate element to be coupled before use with the plunger 11.

The end rim of the container 10 is normally bulged, as shown at 10a, and use is made thereof for strongly fitting on this container 10 a cap 20 with a needle foot 16 of the same type as shown in FIG. 2. After placing said cap 20 on the container end (either just before use or in the factory), a groove in the cap 20 (also present in FIG. 2) snaps on said bulge 10a and then the cap 20 is strongly fixed.

The stopper 12 has an elastic end rim 12a which, as soon as this stopper has been pressed towards the needle end 17 as shown in FIG. 4B, snaps behind the bulge 10a so as to keep the stopper 12 fixed in this position, but the rim 12a is so elastic that the connection can be broken again when the stopper 12 is to be retracted.

The needle end 17, after piercing the stopper 12, extends in the hollow part 12" thereof. The plunger 11 is provided, at its inner side, with a stud 35', e.g. a glass bead embedded in the plunger, which, as soon as it reaches the needle end 17, will bend aside the latter as shown in phantom lines in FIG. 4B. The needle bore will then be closed, so that, when retracting the plunger, the stopper will be pushed inwards by the atmospheric pressure as soon as a (relative) vacuum is created between the plunger 11 and the stopper 12, and also the needle foot 16 will be taken along since the needle end 17 has been bent.

As shown, the in phantom lines in FIG. 4B retracted needle 15 will have a slight inclination. This is caused by bending the needle end 17a since this needle is only supported by the relatively thin central portion 12' of the stopper 12. Moreover the contacting surfaces between the stopper 12 and the needle foot 16 can be given a slight inclination so as to support the inclination of the needle. The operation is, for the rest, the same as in the case of FIG. 2.

Figure 5A:
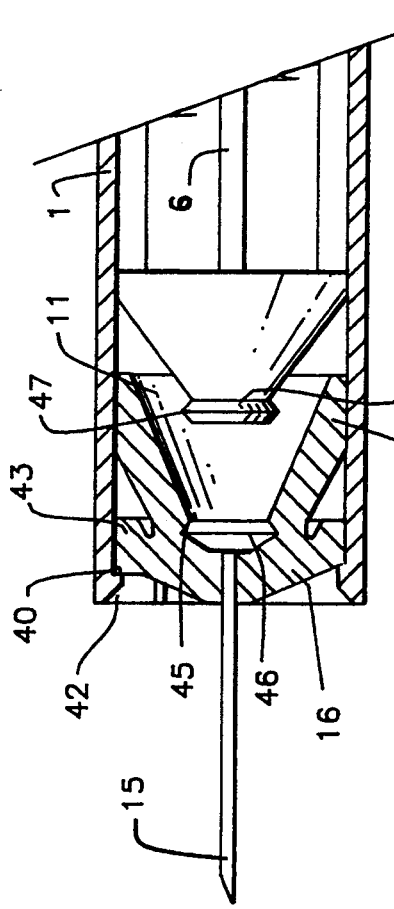

FIGS. 5A and 5B show a different embodiment of the syringe according to the invention. The casing 1 is now also the injection fluid cylinder, which is provide with a plunger 11 and plunger rod 6; the other end of this casing including the atuating member of the plunger rod 6 is not shown for the sake of clarity.

The needle end of the casing 1 is provided with an internal groove 40 with a circular outline adjoining on its outward side an edge 41 with a bevelled inner surface 42.

The syringe further comprises an injection needle 15 which is fixed in a needle foot 16. The needle foot consists of a pliable plastic material and has an outer edge 43 which fits in the groove 40 of the casing 1, but which, as appears from FIG. 5B is formed slightly oval, so that its greatest diameter is approximately equal to the internal diameter of the groove 40. The foot 16 further comprises a sealing lip 44 which lies sealingly against the inner wall of the cylinder formed by the casing 1. The needle foot 16 is thus retained in the groove 40, while the sealing edge 44 provides a liquid tight fit against the cylinder wall.

At the inside of the needle foot 16, there is an inwardly projecting edge 45, which delimits a groove 46, the edge and groove, like the outer edge 43, having an oval shape. The plunger 11 has a slightly widened head portion 47 with a groove 48 behind it, both of which have a circular outline, it being possible to press the head portion 47 into the groove 46. Due to the elasticity of the material of which the foot 16 is made, the groove 46 is then made circular, so that locking of the foot to the head portion 47 takes place. The outer edge 43 of the needle foot is then also made circular, now in such a way, that it is now freed from the groove 40 at its rear end.

The operation of this syringe is as follows. After the plunger 11 is pressed all the way inwards during the injection of the injection fluid, its head 47 engages the groove 46 of the needle foot, which is then coupled to the plunger and freed from the groove 40. If the plunger 11 is then retracted, the needle foot will move inwards with the needle 15, so that the needle 15 is then effectively covered.

In this case also, an additional cap 20 as shown in FIGS. 1 and 2 may be applied, so that after retraction of the needle the latter can be bent onto itself by pushing the plunger outwards and thus making it unusable.

Instead of having the needle foot 16 deformable by the round plunger head portion 47, the wall of the outer casing 1 can be made resiliently deformable, at its needle foot and at least, so that it may be compressed between thumb and index finger in such a way that the edge 43 of the needle foot 16 is freed from the groove 40 which is thereby made oval. In this case, it is also possible to use the sleeve 34 provided with gripping members 35 (see FIG. 3A) instead of the widened head portion 47, the needle 15 then having to project inwardly from the needle foot 16 so as to be gripped by the gripping member 35.

It is also possible to use, for filling the syringe, a special needle with a wider bore which, since it will never contact human body fluids, need not be destroyed. This filling needle can be provided with a simple foot which does not co-operate with the plunger head 47. After filling the syringe, this needle is replaced by an injection needle as shown, which, after use, is retracted and destroyed in the manner described.

FIG. 6 shows a modification of the syringe of FIG. 5, in which parts corresponding with previously mentioned parts have been indicated by the same reference numerals (as the case may provided with primes to indicate a modified shape).

The casing 1 is provided with a narrower end portion 1b having elastic claws 41' with a bevelled end rim 42, allowing a needle foot 16 to be inserted therein and to be gripped by the claws 41', a rim 43'on the foot 16 then snapping in a corresponding groove 40' in the inner wall of the casing end 1b. The needle foot 16 is, furthermore, provided with inwardly extending claws 18'.

The plunger head 47 is, now, also provided with claws 48' which, as shown in the upper half of FIG. 6, will grip the claws 18' of the foot 16, the latter claws then being bent inwardly so that the rim 43' is freed from the groove 40', and the foot can be retracted then together with the plunger 11.

Also in this case a filling needle with a modified foot can be used for filling the syringe, but it is also possible to use a needle foot of the kind as shown with a fitting adapted for mounting therein or thereon needles of different dimensions.

A cap 20 of the type shown in FIGS. 1 and 2 can be used again for destroying the needle after retraction thereof into the casing 1, as described above.

Figure 7B:
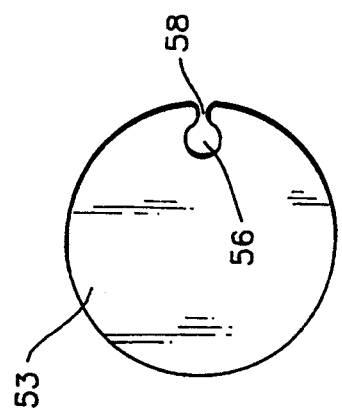
FIGS. 7A and 7B show sections through yet another embodiment of the safety syringe, and a view of a part thereof, respectively.
Figure 7A:
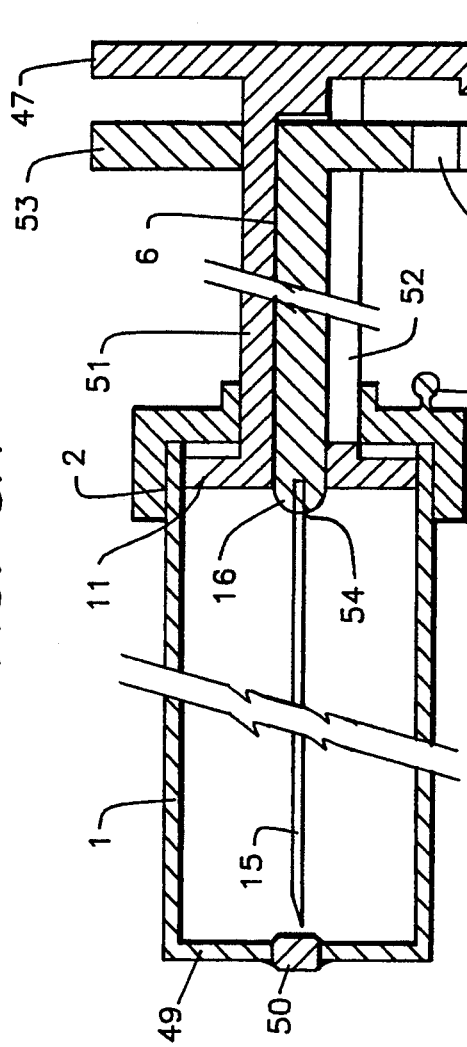

FIG. 7 shows yet another embodiment of the syringe according to the present invention. This once again comprises an outer casing 1, which serves also as an injection fluid cylinder. Its bottom 49 is provided with a closure 50 which may be perforated. The needle 15 is normally inside the casing 1. Its needle foot 16 is now formed as an internal rod projecting through a cavity 51 of the plunger rod 6, the plunger rod further being provided with one or more grooves 52 in order to connect an exterior actuator 53 with said needle foot 16. A passage 54 in the needle foot provides a connection between the inside of the casing 1 and the bore of the needle 15. The casing 1 may be pre-filled with injection fluid, but may also be sucked full after extension of the needle 15.

Prior to use, the actuator 53 is pushed downwards to press the needle 15 out through the closure 50. A lug 55 may then snap into an opening 56 in the actuator 53 so that the actuator is then locked to the casing to prevent retraction of the needle.

After the plunger 11 is pressed downwards, the needle can be retracted together with the plunger 11 by retracting the actuator 53 to make the needle harmless. Again, a cap 20 as shown in FIGS. 1 and 2 may be used to enable the bending onto itself of the needle, while in addition a self-sealing stopper as shown in FIG. 3A may be used.

Is is also possible to provide the actuator knob 7 of the plunger rod 6 with a lug 57, which is bigger than the lug 55, and which widens a groove 58 located to one side of the snapping opening 56 (see FIG. 7A), so that the lug 55 is then freed from the snapping opening 56. In this way, an unequivocal locking between the actuator 53 and the knob 7 is achieved.

Also in the embodiment described with reference to FIG. 5, and in particular the one with a deformable outer wall, the possibility exists of initially providing the needle foot inside the casing and pushing it out prior to use to subsequently lock it, breaking the link with the plunger.

In FIGS. 8A to D a modification of the syringe of FIG. 7 is shown, in which, again, corresponding parts have been indicated by the same reference numerals, as the case may be with primes to indicate a modification thereof.

In this case the rod-shaped needle foot 16 is provided, at its outer end, with a knob 53' lying inside the cavity 51 of the hollow plunger rod 6. Inside this cavity 51 a sleeve 59 with a shoulder 60 can slide on the foot 16. The shoulder 60 co-operates with an elastic latch 61 formed in the wall of the plunger rod 6. The outer diameter of the sleeve 59 is substantially the same as that of the knob 53'.

In the normal position shown in FIG. 8A with retracted needle 15, the latch 61 contacts the sleeve 59.

When pressing the plunger rod 6 downwards, the sleeve 59 will be taken along by the latch 61, and, as soon as the knob 53' engages the bottom of the hollow rod 6, also the needle foot 16 will be taken along so that the needle 15 is pushed outwards, as shown in FIG. 8B. It is also possible to construct the syringe so that already in the initial position shown in FIG. 8A the knob 53' contacts said bottom.

The forward end 47' of the needle foot 16 has a constriction 48' which is gripped then by resilient claws 45', so that, then, the needle foot 16 and, thus, the needle 15, is maintained in its extended position.

Figure 8C:
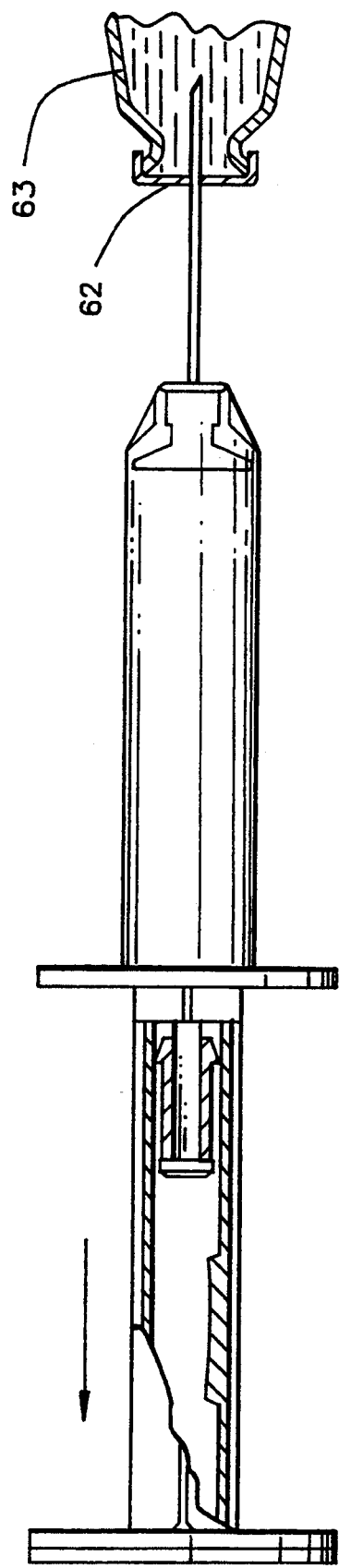
Figure 8D:
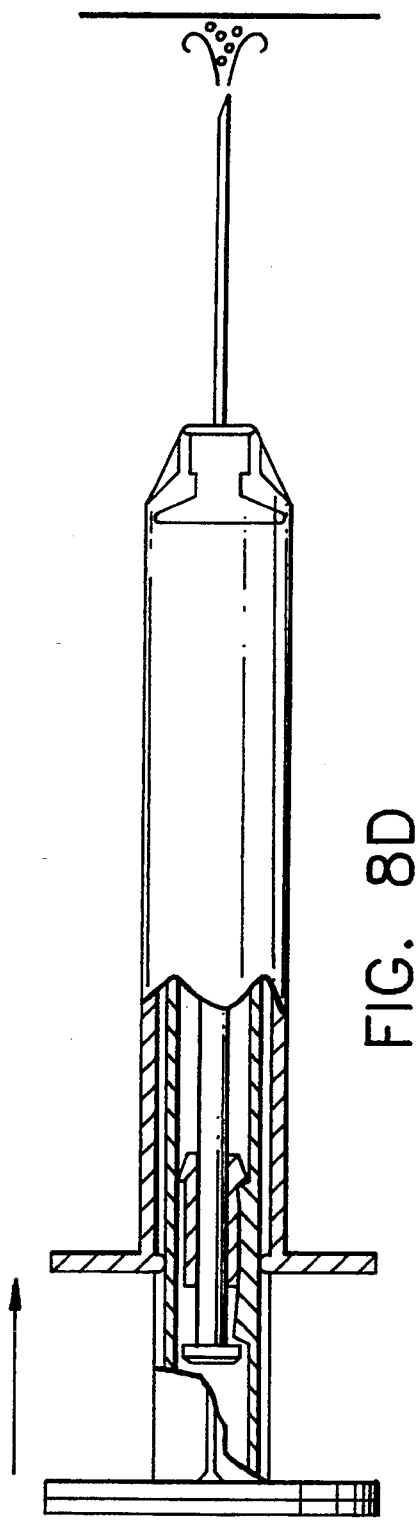

The needle 15 is, then, inserted through the stopper 62 of an injection liquid container 63, as shown in FIG. 8C, whereafter the plunger rod 6 is retracted again for filling the syringe.

When pushing downwards the plunger rod 6, the plunger 11 presses the liquid outwards through the needle. Near the end of the downward stroke, see FIG. 8D, the sleeve 59 is taken along by the latch 61 as the shoulder 60 engages an edge 62 of this latch 61, and then the knob 53' slides along the latch to be gripped by an upper edge 63 of the latter. If, then, the plunger rod 6 is retracted again, the needle is completely retracted into the container 1, and can be destroyed in the manner described before, e.g. by providing a sliding ring 24 in the bottom part 49, or by using a cap 20 as shown in FIG. 2.

The advantage of the construction shown in FIGS. 8A to D is, that only one actuator, viz. the grip 7 of the plunger rod 6, is to be actuated and that it is not possible to actuate the latch 61 from the outside, so that, if the needle would not be destroyed, the syringe cannot be re-used.

FIG. 9 shows still another embodiment of the syringe of the invention, which can be considered as a combination of the syringes of FIGS. 4 and 7. Corresponding parts thereof will, again, be indicated by corresponding reference numerals (with primes as the case may be). The description thereof will be restricted to the essential parts.

This syringe is intended for being filled with injection liquid in the factory, and the needle 15 extending from the container 1 is covered by a needle cap 25, the container 1 being closed by an end cap 20.

The needle foot 16' is, as in FIG. 7, a solid rod, e.g. made of glass, and the needle bore communicated with a hole 54 in the lateral wall of said rod. The outer end of this rod terminates in a knob 34"; claws 8''' of the plunger rod 6 grip behind this knob 34''''. The inner end of the rod 16' is, as in the case of FIGS. 8A to D, provided with a knob 47' cooperating with a resilient seat 45' retaining said rod, and, moreover, providing a sealing so that the passage for the needle 15 in the cap 20 can be made larger.

As in the case of FIG. 4, a stopper 12 is provided, which is held by friction on the rod 16', as is also the plunger 11. When the plunger 11 is pushed inwards and slides, then, along the rod 16', the imcompressible injection liquid will push also the stopper 12 along the rod 16' until it contracts the seat 45' of the cap 20, and the opening 54 is freed, so that the liquid will be pressed through the hollow needle. If the plunger rod 6 is retracted, the plunger 11 will be retracted too because of the vacuum created between the plunger and the plunger rod end, the latter closely fitting within the container 1, so that, again, blood will be sucked inwards if a blood vessel had been hit by the needle tip.

The hollow plunger rod 6 comprises, near its outer end, claws 80 which will grip behind the knob 34" as soon as the plunger 11 has been completely shifted inwards. When retracting the plunger rod 6, the rod 16' will be retracted too, and the needle 15 is completely retracted within the container 1. It can be destroyed thereafter as in the case of the other embodiments.

It will be clear that the elements of the embodiments described above and shown in the drawings can be modified in many ways, and can be used, if necessary in adapted form, also in other embodiments.

I claim:

1. A safety device for an injection syringe comprising:

an elongate casing having a first end and a second end and provided with a longitudinal bore defining an interior surface, said first end adapted to form a substantially fluid tight seal with a cap;

a cap attached to and adapted to form a substantially fluid tight seal with said first end of said elongate casing, said cap provided with a first needle foot engagement means and an aperture for receiving a needle;

a needle foot having a first end and a second end disposed within said longitudinal bore of said elongate casing, said first end of said needle foot provided with a longitudinal bore to fixedly retain a needle, said first end of said needle foot provided with a lateral aperture in the wall of said needle foot in fluid communication with said longitudinal bore of said needle foot, a first needle foot attachment means disposed at said first end of said needle foot, said first needle foot attachment means adapted for selective engagement with said first needle foot engagement means of said cap, a second needle foot attachment means disposed at said second end of said needle foot, said second end of said needle foot adapted for engagement with a plunger means;

a needle having a first end and a second end provided with a longitudinal bore, said second end of said needle attached to and in fluid communication with said longitudinal bore of said first end of said needle foot, said second end of said longitudinal bore of said needle in fluid communication with said lateral aperture in said needle foot, said first end of said needle extending through said aperture in said cap;

a first stopper means slidably disposed around the external surface of said needle foot adapted to form a slidable substantially fluid tight seal with said interior surface of said elongate casing and the external surface of said needle foot, said first stopper means adapted to selectively seal said lateral aperture of said needle foot;

a second stopper means slidable disposed around the external surface of said needle foot between said first stopper means and said second end of said needle foot adapted to form a slidable substantially fluid tight seal with said interior surface of said elongate casing and the external surface of said needle foot, the portion of said longitudinal bore of said elongate casing between said first and said second stopper means defining a chamber for a fluid; and a plunger means having a first end and a second end disposed in said longitudinal bore of said elongate casing, said first end of said plunger means adapted for selective engagement with said second stopper, and said second end of said plunger provided with grasping means for selective engagement with said second needle foot attachment means, said plunger means adapted for reciprocal movement between said first end and said second end of said elongate casing.

2. The safety device of claim 1 further comprising a needle covering means removably attached to said first end of said elongate casing to cover said needle before use.

* * * * *